US006998368B2

(12) United States Patent
Mukkamala

(10) Patent No.: US 6,998,368 B2
(45) Date of Patent: Feb. 14, 2006

(54) CYCLIC NITROXYL COMPOUNDS AS ADDITIVES FOR LUBRICATING OILS

(75) Inventor: Ravindranath Mukkamala, Lansdale, PA (US)

(73) Assignee: Rohm and Haas Company, Philadelphia, PA (US)

(*) Notice: Subject to any disclaimer, the term of this patent is extended or adjusted under 35 U.S.C. 154(b) by 386 days.

(21) Appl. No.: 10/465,209

(22) Filed: Jun. 19, 2003

(65) Prior Publication Data

US 2004/0029745 A1 Feb. 12, 2004

Related U.S. Application Data

(60) Provisional application No. 60/401,537, filed on Aug. 7, 2002.

(51) Int. Cl.
*C10M 135/14* (2006.01)
*C07D 233/42* (2006.01)

(52) U.S. Cl. .................. 508/284; 508/267; 548/316.4
(58) Field of Classification Search ............. 508/284; 548/316.4
See application file for complete search history.

(56) References Cited

U.S. PATENT DOCUMENTS

| 3,532,703 | A | 10/1970 | Murayama et al. ......... 260/294 |
| 3,740,412 | A | 6/1973 | Leute et al. |
| 3,971,757 | A | 7/1976 | Rasberger ............. 260/45.8 N |
| 6,187,722 | B1 | 2/2001 | Rowland et al. ........... 508/284 |
| 6,602,831 | B1 | 8/2003 | Mukkamala ............... 508/284 |
| 6,602,832 | B1 * | 8/2003 | Mukkamala et al. ....... 508/284 |
| 6,734,149 | B1 * | 5/2004 | Mukkamala ............... 508/284 |

FOREIGN PATENT DOCUMENTS

| WO | WO 0107543 | 2/2001 |
| WO | WO 01/62739 A2 | 8/2001 |

OTHER PUBLICATIONS

Derwent Publications Ltd., London, GB: AN 1981-81323D; XP002262369 & SU 802 358 A (Univ Rost); Feb., 7, 1981 Abstract.
Chemical Abstracts Service, Columbus, OH, US: DN: 91: 192432, 1979; Darcy: Free Radical derivatives of . . . retrieved from STN; Database accession No. 1979;592432; XP002262368 Abstract.

* cited by examiner

*Primary Examiner*—Ellen M. McAvoy
(74) *Attorney, Agent, or Firm*—Kenneth Crimaldi

(57) ABSTRACT

A composition comprising: (a) from 0.1% to 20% of at least one cyclic compound having a nitroxyl group and a thioamide group; and (b) a lubricating oil.

10 Claims, No Drawings

CYCLIC NITROXYL COMPOUNDS AS ADDITIVES FOR LUBRICATING OILS

CROSS REFERENCE TO RELATED PATENT APPLICATIONS

This is a non-provisional application of prior pending U.S. provisional application Ser. No. 60/401,537 filed Aug. 7, 2002.

BACKGROUND

This invention relates generally to cyclic nitroxyl compounds useful as anti-oxidant additives for lubricating oil.

Zinc dialkyldithiophosphates (ZDDP) are widely used as lubricant additives to impart anti-wear and anti-oxidant properties. The principal disadvantages of these compounds are that an ash residue is produced by the zinc as the additive is consumed, and that phosphorus is known to affect the efficiency of catalytic converters in motor vehicles, thereby causing emissions problems. Cyclic nitroxyl compounds are disclosed in U.S. Pat. No. 3,532,703 as stabilizers for polyolefins against degradation caused by light. However, this reference does not suggest that such compounds would be useful as additives for lubricating oils, or that a thioamide group would impart useful properties.

The problem addressed by this invention is to find non-metallic oil-soluble anti-oxidant additives for lubricating oils.

STATEMENT OF INVENTION

The present invention is directed to a composition comprising:
(a) from 0.1% to 20% of at least one cyclic compound having a nitroxyl group and a thioamide group; and
(b) a lubricating oil.

The present invention is further directed to a method for improving the anti-oxidant characteristics of a lubricating oil by adding from 0.1% to 20% of at least one cyclic compound having a nitroxyl group and a thioamide group.

The present invention is further directed to a lubricating oil composition containing the reaction product of the cyclic compound having a nitroxyl group and a thioamide group with an imine; an unsaturated carboxylic acid or ester; an isocyanate or isothiocyanate; or an alkyl, alkenyl or aralkyl group bearing a leaving group; and to the aforementioned reaction products themselves.

DETAILED DESCRIPTION

All percentages are weight percentages based on the entire composition described, unless specified otherwise. A "thioamide group" is a functional group containing a thiocarbonyl group bonded to one nitrogen atom; i.e., not including the thiourea group, which has two nitrogen atoms bonded to a thiocarbonyl group. Preferably, a thioamide group has the formula —C(S)—NR—; wherein R is hydrogen, alkyl, alkenyl, aralkyl or aryl; and the thioamide group is not bonded to a nitrogen atom. An "alkyl" group is a saturated hydrocarbyl group having from one to twenty-two carbon atoms in a linear, branched or cyclic arrangement, and having from 0 to 2 oxygen, nitrogen or sulfur atoms. Substitution on alkyl groups of one or more halo, hydroxy, alkoxy, alkanoyl or amido groups is permitted; alkoxy, alkanoyl and amido groups may in turn be substituted by one or more halo substituents. In one preferred embodiment, alkyl groups contain from two to twelve carbon atoms and from 0 to 1 oxygen, nitrogen or sulfur atoms; in another preferred embodiment, alkyl groups contain from 4 to 22 carbon atoms; in another preferred embodiment, alkyl groups contain no heteroatoms. An "alkenyl" group is an "alkyl" group in which at least one carbon-carbon single bond has been replaced with a double bond. An "aryl" group is a substituent derived from an aromatic compound, including heterocyclic aromatic compounds having heteroatoms chosen from among nitrogen, oxygen and sulfur. An aryl group has a total of from five to twenty ring atoms, and has one or more rings which are separate or fused. Substitution on aryl groups of one or more halo, alkyl, alkenyl, hydroxy, alkoxy, alkanoyl or amido groups is permitted, with substitution by one or more halo groups being possible on alkyl, alkenyl, alkoxy, alkanoyl or amido groups. An "aralkyl" group is an "alkyl" group substituted by an "aryl" group. A "lubricating oil" is a natural or synthetic oil, or a mixture thereof, having suitable viscosity for use as a lubricant, e.g., as crankcase oil in an internal combustion engine, automatic transmission fluid, turbine lubricant, gear lubricant, compressor lubricant, metal-working lubricant, hydraulic fluid, etc.

The cyclic compound used in the composition of the present invention has at least one ring, and optionally has acyclic substituents on the ring(s). Each of the nitroxyl and thioamide groups is part of a ring or part of an acyclic substituent. Preferably, the nitroxyl group is part of a ring. Preferably, the thioamide group is part of a ring. Most preferably, each of the nitroxyl group and the thioamide group is part of a ring, either the same ring or different rings. When they are part of different rings, the rings are linked by single or double bonds, or are fused, for example in spiro, fused bicyclic or bridged bicyclic ring systems.

Preferably, the cyclic compound having a nitroxyl group and a thioamide group has at least seven carbon atoms, more preferably at least nine carbon atoms, and most preferably at least twelve carbon atoms. Preferably, the cyclic compound having a nitroxyl group and a thioamide group has at least one substituent which is aryl, aralkyl, alkyl having at least two carbons, or alkenyl having at least four carbons; more preferably at least one substituent is alkyl having at least four carbons.

In a preferred embodiment of the invention, the thioamide and the nitroxyl groups are part of the same five- to eight-membered ring. Preferably the ring is a five- or six-membered ring. In one preferred embodiment the ring is a five-membered ring having formula (I)

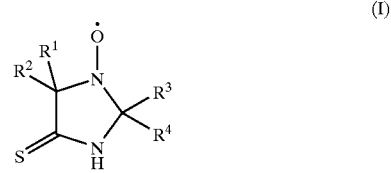

(I)

wherein $R^1$, $R^2$, $R^3$ and $R^4$ independently are hydrogen, alkyl, alkenyl, aryl or aralkyl; or $R^1$ and $R^2$, or $R^3$ and $R^4$, combine with the carbon atom to which they are attached to form an alkyl or alkenyl ring, provided that at least two of $R^1$, $R^2$, $R^3$ and $R^4$ are not hydrogen. Preferably, $R^1$, $R^2$, $R_3$ and $R^4$ independently are alkyl, alkenyl, aryl or aralkyl or $R^1$ and $R^2$, or $R^3$ and $R^4$, combine with the carbon atom to which they are attached to form a $C_5$–$C_8$ alkyl or alkenyl ring; more preferably $R^1$, $R^2$, $R^3$ and $R^4$ independently are alkyl, alkenyl, aryl or aralkyl or $R^1$ and $R^2$, or $R^3$ and $R^4$, combine with the carbon atom to which they are attached to form a $C_5$–$C_6$ alkyl or alkenyl ring. In one embodiment of the invention at least one of $R^1$, $R^2$, $R^3$ and $R^4$ is aryl, aralkyl, $C_2$–$C_{22}$ alkyl or $C_2$–$C_{22}$ alkenyl; more preferably at least one of $R^1$, $R^2$, $R^3$ and $R^4$ is $C_4$–$C_{22}$ alkyl or $C_4$–$C_{22}$ alkenyl; most preferably at least one of $R^1$, $R^2$, $R^3$ and $R^4$ is $C_6$–$C_{22}$ alkyl. Preferably, none of $R^1$, $R^2$, $R^3$ and $R^4$ is hydrogen. The composition of the present invention includes at least one compound of formula (I). In one embodiment of the invention, the composition contains at least two compounds of formula (I), and more preferably contains at least three compounds of formula (I).

In one embodiment of the invention, compounds of formula (I) are produced from known imidazolidinethiones by oxidation, e.g., with hydrogen peroxide or a peracid, as shown below in Scheme 1.

Scheme 1

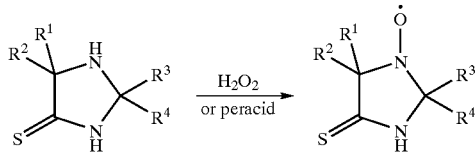

In another preferred embodiment, the ring is a six-membered ring having formula (II)

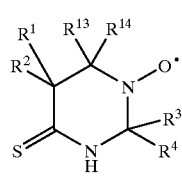

(II)

wherein $R^{13}$ and $R^{14}$ independently are alkyl, alkenyl, aryl or aralkyl or $R^{13}$ and $R^{14}$ combine with the carbon atom to which they are attached to form a $C_5$–$C_8$ alkyl or alkenyl ring; more preferably $R^{13}$ and $R^{14}$ independently are alkyl, alkenyl, aryl or aralkyl or $R^{13}$ and $R^{14}$ combine with the carbon atom to which they are attached to form a $C_5$–$C_6$ alkyl or alkenyl ring. As described herein for the five-membered ring analog, the compound of formula (II) is produced from known compounds by oxidation of a secondary amino group.

In another preferred embodiment, the nitroxyl group and the thioamide group are in the same ring of a bicyclic compound, for example, the compound having formula (III)

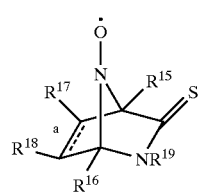

(III)

wherein $R^{15}$ and $R^{16}$ independently are alkyl, alkenyl, aryl or aralkyl; $R^{17}$ and $R^{18}$ independently are hydrogen, alkyl, alkenyl, aryl or aralkyl; $R^{19}$ is hydrogen, alkyl, alkenyl, aryl, aralkyl, alkanoyl or aroyl; and bond "a" is a single or double bond. In one embodiment of the invention at least one of $R^{15}$, $R^{16}$, $R^{17}$, $R^{18}$, and $R^{19}$ is aryl, aralkyl, $C_4$–$C_{22}$ alkyl or $C_4$–$C_{22}$ alkenyl; more preferably at least one of $R^{15}$, $R^{16}$, $R^{17}$, $R^{18}$, and $R^{19}$ is $C_4$–$C_{22}$ alkyl or $C_4$–$C_{22}$ alkenyl; and most preferably at least one of $R^{15}$, $R^{16}$, $R^{17}$, $R^{18}$, and $R^{19}$ is $C_6$–$C_{22}$ alkyl. In one embodiment of the invention, a compound of formula (III) in which bond "a" is a double bond is prepared, for example, by the cycloaddition reaction of an isothiocyanate and a substituted pyrrole, as shown below in Scheme 2, followed by oxidation of the secondary amino group in the product.

Scheme 2

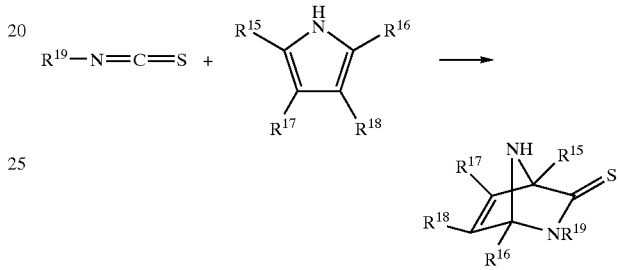

$R^{19}$ is alkyl, alkenyl, aryl or aralkyl; preferably, $R^{19}$ is $C_6$–$C_{22}$ alkyl, $C_6$–$C_{22}$ alkenyl, aryl or aralkyl; more preferably $R^{19}$ is $C_6$–$C_{22}$ alkyl or aryl; most preferably $R^{19}$ is $C_8$–$C_{22}$ alkyl. In another embodiment in which bond "a" is a single bond, the compound of formula (III) is prepared as shown, for example, in Scheme 3, followed by oxidation of the secondary amino group in the product.

Scheme 3

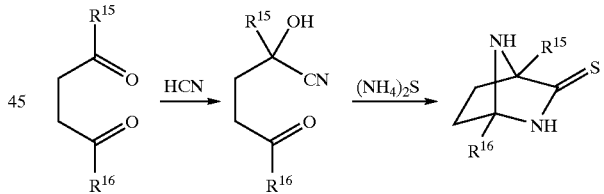

In another preferred embodiment, the nitroxyl group and the thioamide group are in different five- to eight-membered rings. In one embodiment in which the nitroxyl group is part of a six-membered ring and the thioamide is part of a five-membered ring, the compound has formula (IV)

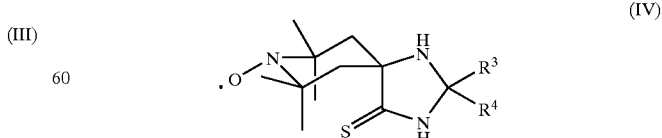

(IV)

wherein $R^3$ and $R^4$ independently are hydrogen, alkyl, alkenyl, aryl or aralkyl; or $R^3$ and $R^4$ combine with the carbon atom to which they are attached to form an alkyl or alkenyl ring, provided that at least one of $R^3$ and $R^4$ is not hydrogen. Preferably, at least one of $R^3$ and $R^4$ is aryl, aralkyl, $C_4$–$C_{22}$ alkyl or $C_4$–$C_{22}$ alkenyl.

In one embodiment of the invention, compounds of formula (IV) are produced as shown below in Scheme 4.

Scheme 4

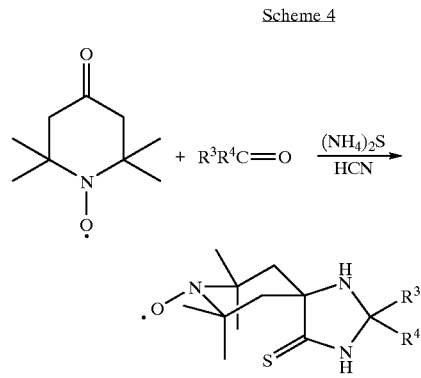

In a preferred embodiment of the invention, the thioamide group, or a primary or secondary amino group, of the cyclic compound having a nitroxyl group and a thioamide group is further functionalized by reaction with imines of formula $R^5N=CR^6R^7$; unsaturated carboxylic esters of formula $CHR^8=CR^9COOR^{10}$; an isocyanate, $R^{12}NCO$, or an isothiocyanate, $R^{12}NCS$; or $R^{11}X$; wherein $R^6$, $R^7$ and $R^{10}$ independently are hydrogen, alkyl, alkenyl, aryl or aralkyl; $R^{11}$ is alkyl, alkenyl or aralkyl; $R^8$ and $R^9$ independently are hydrogen or $C_1$–$C_4$ alkyl; $R^5$ and $R^{12}$ independently are alkyl, alkenyl, aryl or aralkyl; and X is a suitable leaving group capable of being displaced by the nitrogen or the sulfur of a thioamide group, e.g., iodide, bromide, chloride, tosylate, mesylate or triflate. Functionalization of the thioamide group can occur on the thioamide nitrogen or the thioamide sulfur, provided of course that the thioamide nitrogen bears at least one hydrogen. The product also can be a mixture of the compound functionalized on the nitrogen and the one functionalized on the sulfur.

Preferably, $R^8$ and $R^9$ independently are hydrogen or methyl. Preferably, $R^8$ is hydrogen. Preferably, the compound of formula $CHR^8=CR^9COOR^{10}$ is an alkyl or aralkyl acrylate having $R^8=R^9=H$ and $R^{10}$=alkyl or aralkyl; or a methacrylate ester having $R^8=H$ and $R^9=CH_3$; or a crotonate ester having $R^9=H$ and $R^8=CH_3$. Preferably, $R^{10}$ is alkyl or aralkyl, most preferably $C_4$–$C_{22}$ alkyl. Preferably, $R^5$ is $C_{12}$–$C_{22}$ alkyl. In one embodiment, $R^5$ is derived from an unsubstituted $C_{16}$–$C_{22}$ alkyl amine, $R^5NH_2$, preferably one which is an oil-soluble amine. In one embodiment, the alkyl amine is a tertiary alkyl primary amine, i.e., a primary amine in which the alkyl group is attached to the amino group through a tertiary carbon. Examples of commercially available tertiary alkyl primary amines are the Primene™ amines available from Rohm and Haas Company, Philadelphia, Pa. Preferably, $R^6$ and $R^7$ independently are alkyl or hydrogen. In a preferred embodiment of the invention, $R^5N=CR^6R^7$ is a formaldehyde imine, $R^5N=CH_2$. Preferably, $R^{11}$ is $C_4$–$C_{22}$ alkyl, $C_4$–$C_{22}$ alkenyl or aralkyl; more preferably $C_6$–$C_{22}$ alkyl or $C_6$–$C_{22}$ alkenyl; and most preferably $C_8$–$C_{22}$ alkyl. Preferably $R^{12}$ is alkyl, aryl or aralkyl, most preferably $C_8$–$C_{22}$ alkyl.

As an example, the reaction of the compound of formula (I), having no primary or secondary amine nitrogen atoms, with an imine and an acrylate is illustrated below in Scheme 5. Analogous products result from reaction of the compounds of formula (II), formula (III) or formula (IV) with an imine or an acrylate.

Scheme 5

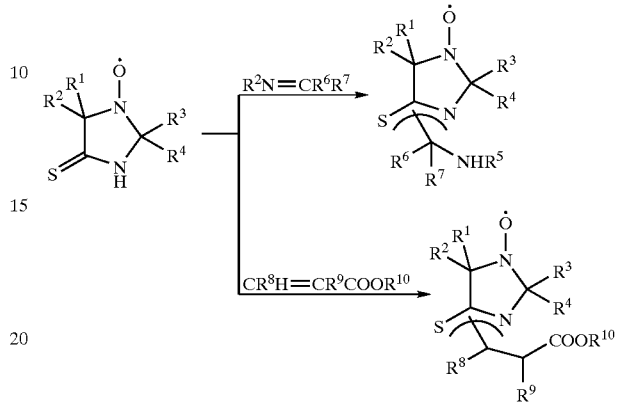

The compound resulting from functionalization of the thioamide group in the compound of formula (I) on sulfur or nitrogen can be represented by formula (Va) or (Vb), respectively.

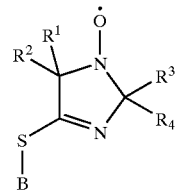
(Va)

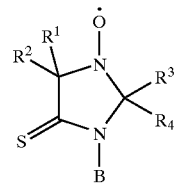
(Vb)

wherein B is $-CR^8H-CR^9H-COOR^{10}$, $-CR^6R^7NHR^5$, $-C(O)NHR^{12}$, $-C(S)NHR^{12}$ or $R^{11}$. Possibly, a particular combination of functionalizing reagent and substitution on the ring will result in a mixture of N- and S-substitution.

The compound resulting from functionalization of the thioamide group in the compound of formula (IV) on sulfur or nitrogen can be represented by formula (VIa) or (VIb), respectively.

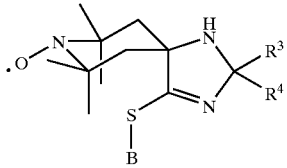
(VIa)

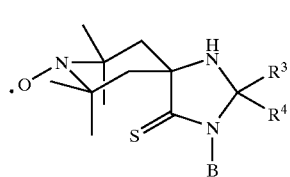

The compound resulting from functionalization of the thioamide group in the compound of formula (II) on sulfur or nitrogen can be represented by formula (VIIa) or (VIIb), respectively.

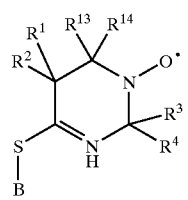

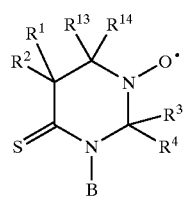

The compound resulting from functionalization of the thioamide group in the compound of formula (III), in which $R^{19}$ is hydrogen, on sulfur or nitrogen can be represented by formula (VIIIa) or (VIIIb), respectively.

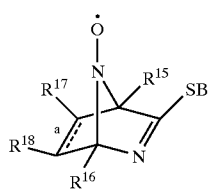

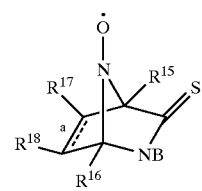

In addition to compounds (V), (VI), (VII) and (VIII), other functionalized thioamides derived from the cyclic compound having a nitroxyl group and a thioamide group are possible, as will be apparent to one skilled in the art. Compounds functionalized on primary or secondary amino groups that are present in the cyclic compound also are possible.

Preferably, the cyclic compound(s) containing a nitroxyl group and a thioamide group is present in a lubricating oil in a total amount of at least 0.2%, more preferably at least 0.3%, and most preferably at least 0.4%. Preferably, the compound(s) is present in a lubricating oil in a total amount no greater than 10%, more preferably no greater than 5%, and most preferably no greater than 2%. Preferably, the compounds are soluble at the aforementioned levels.

Optionally, other additives typically used in lubricating oils are present in the composition. Such additives include, but are not limited to, other antioxidants, anti-wear additives, anti-corrosion additives, dispersants, detergents, anti-foamants, friction modifiers, seal swell agents, demulsifiers, viscosity index improvers and pour point depressants. Anti-wear additives that can be used in combination with the cyclic compound(s) containing a nitroxyl group and a thioamide group include the commercial products known as ZDDP, which are zinc dialkyldithiophosphates. In addition to acting as an antioxidant in lubricating oils, the compound of formula (I) typically also improves the anti-wear and anti-corrosion characteristics of lubricating oil.

What is claimed is:

1. A composition comprising:
   (a) from 0.1% to 20% of at least one cyclic compound having a nitroxyl group and a thioamide group; and
   (b) a lubricating oil.

2. The composition of claim 1 in which the nitroxyl group and the thioamide group are part of the same five- to eight-membered ring.

3. The composition of claim 2 in which said at least one cyclic compound has formula (I)

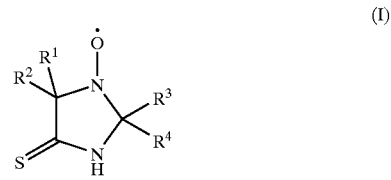

wherein $R^1$, $R^2$, $R^3$ and $R^4$ independently are hydrogen, alkyl, alkenyl, aryl or aralkyl; or $R^1$ and $R^2$, or $R^3$ and $R^4$, combine with the carbon atom to which they are attached to form an alkyl or alkenyl ring, provided that at least two of $R^1$, $R^2$, $R^3$ and $R^4$ are not hydrogen.

4. The composition of claim 3 in which at least one of $R^1$, $R^2$, $R^3$ and $R^4$ is aryl, aralkyl, $C_4$–$C_{22}$ alkyl or $C_4$–$C_{22}$ alkenyl; and none of $R^1$, $R^2$, $R^3$ and $R^4$ is hydrogen.

5. The composition of claim 1 in which said at least one cyclic compound has formula (IV)

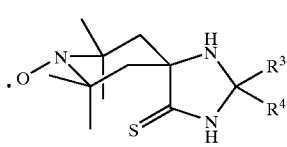

wherein $R^3$ and $R^4$ independently are alkyl, alkenyl, aryl or aralkyl; or $R^3$ and $R^4$ combine with the carbon atom to which they are attached to form an alkyl or alkenyl ring.

6. The composition of claim 5 in which at least one of $R^3$ and $R^4$ is aryl, aralkyl, $C_4$–$C_{22}$ alkyl or $C_4$–$C_{22}$ alkenyl.

7. A composition produced by mixing:

(a) a reaction product of: (i) a cyclic compound having a nitroxyl group and a thioamide group; and (ii) one of: $R^5N{=}CR^6R^7$, $CHR^8{=}CR^9COOR^{10}$, $R^{12}NCO$, $R^{12}NCS$, or $R^{11}X$; wherein $R^6$, $R^7$ and $R^{10}$ independently are hydrogen, alkyl, alkenyl, aryl or aralkyl; $R^{11}$ is alkyl, alkenyl or aralkyl; $R^8$ and $R^9$ independently are hydrogen or $C_1$–$C_4$ alkyl; $R^5$ and $R^{12}$ independently are alkyl, alkenyl, aryl or aralkyl; and X is a suitable leaving group; and (b) a lubricating oil.

8. The composition of claim 7 in which the cyclic compound reacts with an imine of formula $R^5N{=}CR^6R^7$.

9. The composition of claim 8 in which $R^5$ is $C_{12}$–$C_{22}$ alkyl.

10. A compound having formula

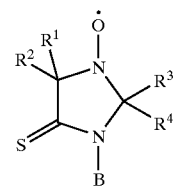

wherein $R^1$, $R^2$, $R^3$ and $R^4$ independently are alkyl, alkenyl, aryl or aralkyl; or $R^1$ and $R^2$, or $R^3$ and $R^4$, combine with the carbon atom to which they are attached to form a $C_5$–$C_8$ alkyl or alkenyl ring; B is —$CR^8H$—$CR^9H$—$COOR^{10}$, —$CR^6R^7NHR^5$, —$C(O)NHR^{12}$ or —$C(S)NHR^{12}$; $R^6$, $R^7$ and $R^{10}$ independently are hydrogen, alkyl, alkenyl, aryl or aralkyl; $R^8$ and $R^9$ independently are hydrogen or $C_1$–$C_4$ alkyl; $R^5$ and $R^{12}$ independently are alkyl, alkenyl, aryl or aralkyl.

* * * * *